United States Patent
Hughes et al.

(10) Patent No.: US 11,221,406 B2
(45) Date of Patent: Jan. 11, 2022

(54) GUIDED WAVE RADAR FOR CONSUMABLE PARTICLE MONITORING

(71) Applicant: Honeywell International Inc., Morris Plains, NJ (US)

(72) Inventors: Michael Kon Yew Hughes, Vancouver (CA); Daliah Papoutsis, Glenview, IL (US); Jonathan Andrew Tertel, Mt. Prospect, IL (US); Randall E. Holt, Elgin, IL (US)

(73) Assignee: Honeywell International Inc., Charlotte, NC (US)

( * ) Notice: Subject to any disclaimer, the term of this patent is extended or adjusted under 35 U.S.C. 154(b) by 688 days.

(21) Appl. No.: 15/590,504

(22) Filed: May 9, 2017

(65) Prior Publication Data
US 2018/0328769 A1 Nov. 15, 2018

(51) Int. Cl.
*G01S 13/88* (2006.01)
*G01F 23/284* (2006.01)
*G01N 33/28* (2006.01)

(52) U.S. Cl.
CPC ............ *G01S 13/88* (2013.01); *G01F 23/284* (2013.01); *G01N 33/2823* (2013.01)

(58) Field of Classification Search
CPC ................... G01F 1/74; G01F 1/76–90; G01F 23/284–2928
See application file for complete search history.

(56) References Cited

U.S. PATENT DOCUMENTS

| | | | |
|---|---|---|---|
| 2,804,940 A * | 9/1957 | Hutchinson | B01D 53/26 95/91 |
| 5,330,618 A | 7/1994 | Daniels et al. | |
| 5,644,010 A | 7/1997 | Kurihashi et al. | |
| 5,972,669 A | 10/1999 | Harz et al. | |
| 6,178,817 B1 | 1/2001 | Hewelt et al. | |
| 6,280,694 B1 | 8/2001 | Mason | |
| 6,410,783 B1 | 6/2002 | Peterson et al. | |
| 6,979,426 B2 | 12/2005 | Teall et al. | |
| 7,011,800 B1 | 3/2006 | Mason | |
| 7,125,531 B1 | 10/2006 | Mason | |
| 7,219,500 B1 | 5/2007 | Rhodes | |

(Continued)

OTHER PUBLICATIONS

The Engineer's Guide to Level Measurement, Emerson Electric Co, 2020, chapter 1, pp. 10-30 (Year: 2020).*

(Continued)

*Primary Examiner* — Brent A. Fairbanks
(74) *Attorney, Agent, or Firm* — Ortiz & Lopez, PLLC; Kermit D. Lopez; Luis M. Ortiz

(57) ABSTRACT

Method and apparatus for monitoring amounts of submerged solid consumable. A GWR (Guided Wave Radar) component can provide a measurement of a reflection at a fixed position in a particle bed. The reflection represents aggregate dielectric properties in a vessel. The measurement includes hydrocarbon and solid consumable properties of a mixture in the vessel, wherein a measurement value is indicative of a greater amount of the solid consumable in the mixture in the vessel. If data is measured by the GWR component indicating that the measurement value is approaching the measurement value of the hydrocarbon, this data is indicative that the material (e.g., solid consumable such as salt) in the vessel should be replenished.

16 Claims, 7 Drawing Sheets

(56) References Cited

U.S. PATENT DOCUMENTS

| | | | |
|---|---|---|---|
| 7,452,515 | B1 | 11/2008 | Lafleur et al. |
| 7,491,861 | B2 | 2/2009 | Mason |
| 7,531,152 | B2 | 5/2009 | Mason |
| 7,763,219 | B2 | 7/2010 | Mason |
| 7,871,448 | B2 | 1/2011 | Jackam et al. |
| 7,924,216 | B2 | 4/2011 | Delin |
| 8,080,087 | B2 | 12/2011 | Falkiner et al. |
| 8,088,183 | B2 | 1/2012 | Jackam et al. |
| 8,524,854 | B2 | 9/2013 | Chiong et al. |
| 8,728,177 | B2 | 5/2014 | Jackam et al. |
| 2009/0133577 | A1* | 5/2009 | Falkiner ............ C10G 33/04 95/152 |
| 2010/0327884 | A1* | 12/2010 | McCall ............ F01N 3/2066 324/682 |
| 2013/0319022 | A1* | 12/2013 | Becze ............ B01D 53/18 62/94 |
| 2013/0320145 | A1 | 12/2013 | McGillis et al. |
| 2014/0026749 | A1* | 1/2014 | Becker ............ B01D 53/261 95/91 |
| 2015/0084809 | A1 | 3/2015 | Flasza et al. |
| 2015/0276460 | A1 | 10/2015 | Georgescu et al. |
| 2015/0321897 | A1 | 11/2015 | Lurcott et al. |
| 2016/0097669 | A1 | 4/2016 | Backstrom et al. |
| 2016/0097670 | A1 | 4/2016 | Hughes et al. |
| 2016/0266240 | A1 | 9/2016 | Hughes et al. |
| 2016/0320223 | A1 | 11/2016 | Heath et al. |
| 2019/0025234 | A1* | 1/2019 | Weightman ........ G01N 33/2823 |
| 2019/0323936 | A1* | 10/2019 | Allouche ............ G01N 13/00 |

OTHER PUBLICATIONS

Firmware—Wikipedia, printed Apr. 27, 2017, 6 pages.
Extended European Search Report for corresponding EP Application No. 18798054.5, dated Dec. 10, 2020.

* cited by examiner

GUIDED WAVE RADAR FOR CONSUMABLE PARTICLE MONITORING

TECHNICAL FIELD

Embodiments are related to the field of hydrocarbon processing. Embodiments also relate to salt dryers utilized for drying fluid steams and solid caustic beds for removing acids in hydrocarbon processing operations. Embodiments further relate to the drying of hydrocarbon streams in petroleum refineries, terminals, and other processing plants. Embodiments additionally relate to GWR (Guided Wave Radar) components and measuring techniques including GWR transmitters and probes.

BACKGROUND

Significant amounts of water can become mixed with hydrocarbon streams during production and processing. Petroleum refinery streams, for example, may be treated with water, steam, or various aqueous solutions during processing in order to carry out the processing and to meet various quality specifications. Steam stripping, caustic treating, and amine treating are frequently used in conventional refinery processing and although much of the water introduced in this way can be removed by simple settling procedures, a certain amount of water remains dissolved in the fuel or entrained in the fuel as small droplets after removal of the bulk of the water.

Excess amounts of water frequently adversely affect the properties and quality of hydrocarbon fuels, for example, by creating haze in fuels which would otherwise be clear, accelerating rust and other forms of corrosion on containers and equipment, and by the formation of ice crystals at low temperatures which may lead to plugging of filters and other equipment, for example, fuel lines and injectors. Water may also contain contaminants such as acids which may lead to accelerated corrosion. It is therefore usually necessary to reduce the amount of any remaining water from petroleum fuels and other products in order to meet various product specifications; the separation may be carried out at the refinery, at the distribution terminal, or at the location of use, for example, an airport. Note that salt does not remove all of the dissolved water, but only approximately 30% of (along with all of the entrained water).

One method for separation involves the use of a salt dryer, which is a drying unit that contains a dehydrating solid compound which combines with the water in the liquid to from an aqueous solution which can be separated from the gas flowing through the unit. Salt dryers are capable of removing both free water, i.e., water which is suspended in the form of droplets in the hydrocarbon, as well as dissolved water and for this reason, are capable of bringing the residual water content of hydrocarbon streams down to the levels set by product specifications or by processing requirements. Salt dryers typically use dehydrating salts such as sodium chloride, calcium chloride, sodium sulfate, sodium hydroxide, potassium hydroxide, lithium bromide, or lithium chloride for this purpose. Of these, the lithium salts are the most effective, being capable of reducing the water content of most hydrocarbon streams to about 10-20% relative saturation level, but the lithium salts are expensive and normally the purchase and disposal cost is not warranted in large scale commercial units.

For some hydrocarbon processes, such as in kerosene or diesel production, it is necessary to remove water from the product. This is done by absorption by salt in the salt dryers. The absorbed water can be removed as brine from the bottom of the vessel. It is difficult to determine the level of salt in the vessel while it is in operation. Commonly, the vessels are bypassed and the hydrocarbon is removed before being opened for inspection which is costly. A measurement of the amount of salt in the vessel could save a lot of money by reducing the frequency of process shutdowns.

As the salt is dissolved, its packed density may be reduced, reducing its effective dielectric constant. Additionally, salt settling in the vessel may create an uneven surface. These two effects can combine to make the salt surface undetectable. In some situations, caustic washes are employed in alkylation plants. The use is similar to the above described implementations except that caustics (e.g., KOH or NaOH, caustic soda, and caustic potash) are used instead of salt. These materials will react with residual acids to produce spent caustic (instead of brine) while dissolving the caustic. This method will be applied when using a solid caustic (e.g., most often KOH), as a liquid caustic wash does not need this same detection method.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an, improved method, apparatus, and system for measuring the properties of a mixture of hydrocarbons and dissolvable solids (e.g., salt, solid caustic) in a vessel.

It is another aspect of the disclosed embodiments to provide for a method, apparatus, and system for monitoring amounts of submerged solid consumable.

It is also an aspect of the disclosed embodiments to provide for a measurement method and apparatus device for use in hydrocarbon processing operations.

It is yet another aspect of the disclosed embodiments to provide for a GWR measurement component for use with salt dryers utilized for drying fluid streams in hydrocarbon processing operations.

The aforementioned aspects and other objectives and advantages can now be achieved as described herein. Methods, systems, and devices are disclosed for monitoring amounts of submerged solid consumable. In an example embodiment, a GWR component provides a measurement of a reflection at a fixed position in a particle bed such that the reflection represents aggregate dielectric properties in a vessel, wherein the measurement includes hydrocarbon and solid consumable properties of a mixture in the vessel. The measurement value of the measurement is indicative of a greater amount of solid consumable in the mixture in the vessel. If data is measured by the GWR component indicating that the measurement value is approaching the measurement value of the hydrocarbon, such data indicative that the material in the vessel should be replenished.

The aforementioned hydrocarbon can be, for example, a hydrocarbon such as kerosene, diesel, naphtha, and LPG (Liquefied Petroleum Gas). The solid consumable can be, for example, salt containing sodium chloride, potassium chloride, calcium chloride, or lithium chloride, or a combination thereof. In other example embodiments, the hydrocarbon can be, for example, butane, propane, or alkylates and the mixture can be, for example, sodium, hydroxide, potassium hydroxide, or calcium hydroxide. In some example embodiments, the vessel may be a salt dryer.

The effective refractive index in the vessel can therefore be measured with a GWR (Guided Wave Radar) component. The measured effective refractive index includes an effective refractive index of hydrocarbon and salt properties of a mixture in the vessel, wherein a measured higher refractive index is indicative of a greater amount of salt in the mixture in the vessel, and wherein if data is measured by the GWR component indicating that the refractive index approaches a refractive index of the hydrocarbon, the data is indicative that the salt in the vessel should be replenished.

The effective refractive index of the properties of the hydrocarbon/salt mixture in the vessel is thus measured with the GWR component (e.g., a GWR probe). That is, the more salt in the vessel, the higher the refractive index. When the refractive index approaches that of the hydrocarbon (e.g., kerosene) by itself, it is time to replenish the salt. If it is desired that the salt should be replenished when the level drops by 50% so that there is still effective water removal, the replenishment can be triggered when the measured effective refractive index is at a level predetermined to correspond to a 50% salt level. Transmitter firmware can be utilized to identify the echo from the end of the GWR probe. This will be at a position n×L, where n is the average refractive index and L is the true probe length. Knowing the properties of, for example, kerosene and salt, the amount of salt in the vessel can be calculated as discussed in greater details herein.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the embodiments to those skilled in the art. As used herein, the term "and/or" includes any and all combinations of one or more of the associated listed items.

Reference will be made in detail to the disclosed embodiments (exemplary embodiments) of the invention, examples of which are illustrated in the accompanying drawings, and which may be preferred or alternative embodiments. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising," The term "at least one of" is used to mean one or more of the listed items can be selected.

Figure 1:
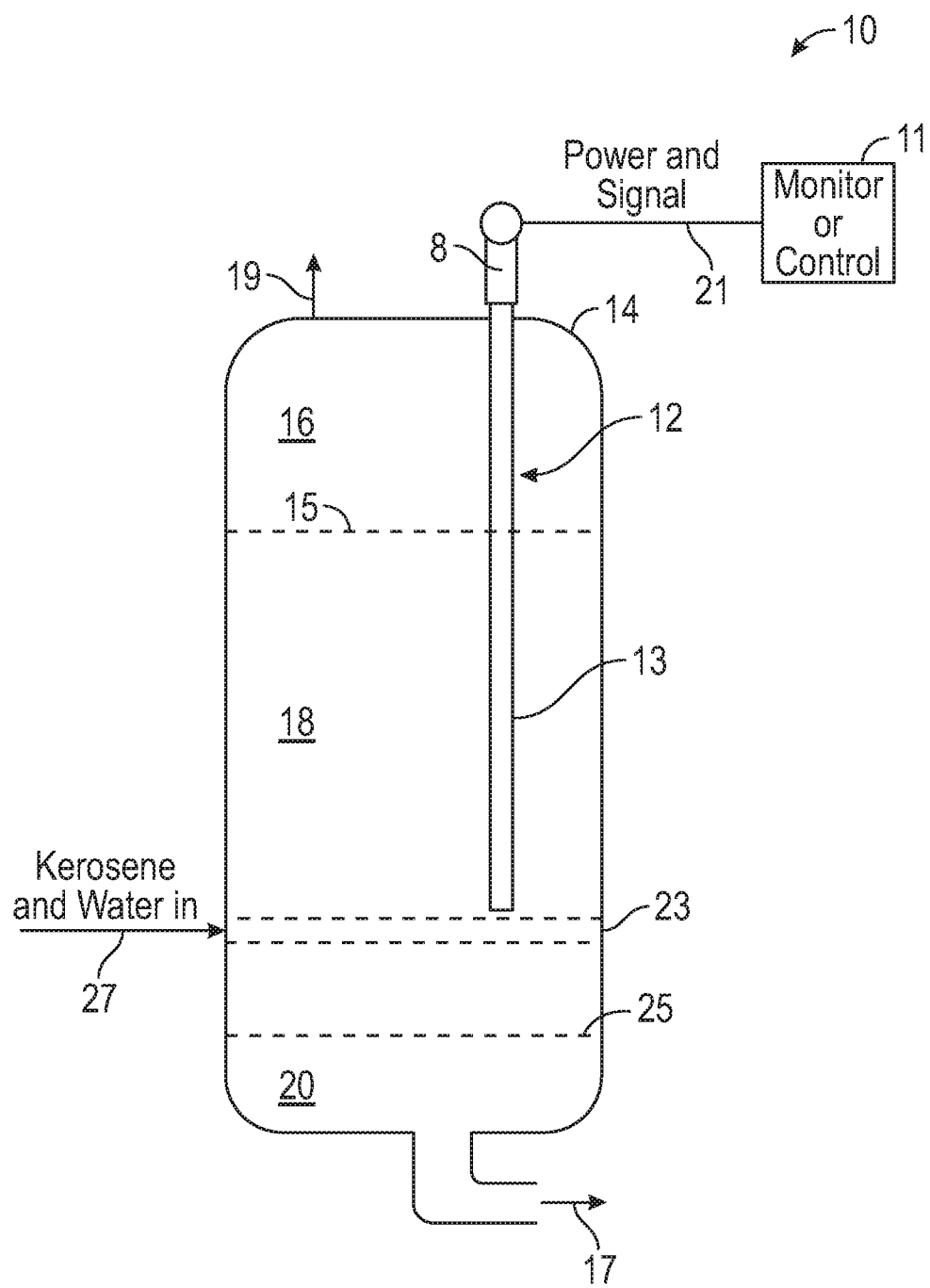
FIG. 1 illustrates a schematic diagram of an apparatus for measuring the properties of a mixture of salt and hydrocarbon in a vessel utilized in a hydrocarbon processing operation, in accordance with an example embodiment.

FIG. 1 illustrates a schematic diagram of a system 10 for measuring the properties of a mixture of a hydrocarbon (e.g., kerosene) and a solid consumable (e.g., a dissolvable solid such as salt, a caustic solid, etc.) in a vessel 14 utilized in a hydrocarbon processing operation, in accordance with an example embodiment. The system 10 can be utilized for salt dryer monitoring and generally includes the vessel 14 and a GWR component 12 composed of a GWR transmitter 8 and a GWR probe 13. The GWR probe 13 extends into an interior central portion 18 of the vessel 14. The GWR transmitter 8 can transmit data to a monitoring or control system 11. In some example embodiments, this can be accomplished with, for example, a 4-20 mA signal; but can also be accomplished with wired digital protocols such as HART™, FIELDBUS™, or with wireless protocols such as ISA100 Wireless. The line 21 shown in FIG. 1 is representative of power and communications (e.g., power+signal)

between the monitor/control system 11 and the GWR transmitter 8. The vessel 14 can also include a kerosene distributor 23 as shown in FIG. 1 with respect to the arrow 27 (which indicates entry of kerosene and water into the vessel 14).

The central portion 18 of the vessel 14 shown in FIG. 1 is disposed between an upper portion 16 and the kerosene distributor 23. The upper portion 16 contains a hydrocarbon only such as kerosene. The interior portion 18 can contain a mixture of the hydrocarbon (in this example, kerosene) and a solid consumable such as a coarse salt (in this example sodium chloride) which can be supported on a support or screen 25 through which brine can drain from the lower portion 20 of the vessel 14, as indicated by arrow 17 in FIG. 1. The screen 25 is located above the lower portion 20 of the vessel 14. Note that in some example embodiments, such as the case with a Merox unit, the salt is not typically supported on a screen, but fills the bottom of the vessel including the bottom head.

The GWR probe 13 extends into the vessel 14 through the upper portion 16 and into the interior portion 18. Kerosene can be introduced near the bottom of the salt bed as indicated by arrow 27 and then removed from the top of the vessel 14 as indicated by the arrow 19. That is, the arrow 19 is representative of dry kerosene exiting the vessel 14. Note that the end of the probe 13 can be placed above any objects, which may interfere with the measurement such as screens or distributors. Note that although some of the example embodiments described herein refer to the use of kerosene as the hydrocarbon of interest, it can be appreciated that other types of hydrocarbons can also be tested and measured in accordance with the disclosed embodiments. For example, diesel may be a hydrocarbon of interest.

The GWR component 12 can be utilized to measure the effective refractive index in the vessel 14. The refractive index measured includes the index of the salt/kerosene mixture 18 properties. A measured higher refractive index indicates that a greater amount of salt is in the mixture in the vessel 14. If, however, the measured data reveals that the refractive index is approaching the refractive index of the hydrocarbon (i.e., Kerosene), this data indicates that the salt in the vessel should be replenished. The vessel 14 itself may comprise a component or a part of a salt dryer device or system. Note that with some salt/hydrocarbon mixtures, the refractive index of the salt may be lower than that of the hydrocarbon and therefore a vessel full of salt would have a lower aggregate index of refraction.

In some example embodiments, the GWR component 12 and/or the GWR transmitter 8 can be configured to measure the level of salt in a salt dryer vessel such as vessel 14. The vessel 14 is filled with salt, which gradually dissolves when contacting water in the kerosene. The salt surface 15 is shown FIG. 1 above the interior portion 18. The kerosene enters near the bottom of the salt bed contained in the vessel 14 as indicated by arrow 27 and exits the top of the vessel 14 as indicated by arrow 19. The flow rate of kerosene is very slow and the vessel 14 is completely filled. The brine flows to the bottom of the vessel 14 due to its density, which is greater than that of the hydrocarbon. The salty water (brine) is drained off the bottom of the vessel 14 as indicated by arrow 17. The brine may be drained either automatically via liquid interface level control (not shown) or manually several times a day. The quantity that may be measured using the system 10 is the quantity of the salt in the vessel 14. Note that if the density of the salt is reduced, then it is the mass of salt that is being measured.

The average refractive index of the properties of the hydrocarbon/salt mixture in the central or interior portion 18 of the vessel 14 can be measured with a GWR component such as a GWR probe. That is, the more salt in the vessel, the higher the refractive index. When the refractive index approaches that of the hydrocarbon (e.g., kerosene) by itself, it is time to replenish the salt. Transmitter firmware can be utilized to identify the echo from the end of the GWR probe. This will be at a position $n \times L$, where n is the average refractive index and L is the true probe length. Knowing the properties of, for example, kerosene, salt, and their mixture, the amount of salt in the vessel can be calculated. This can be described as an equivalent level, a volume, or a mass.

Note that in some example embodiments, instead of having the output configured as a quantity, measurement limits can be set on the device and the output can be in the form of a 4-20 mA output, corresponding to the full range, for example, 3.8 to 4.0 mA corresponding to the vessel with salt at a level near the end of the probe and 20.0 to 20.8 mA for a full vessel. A current set point (e.g., 12 mA) can be defined such that when the current reaches that value, it is time to refill the vessel. Measurement levels can be set or a trend plot analyzed such that a process shutdown and salt addition can be scheduled. It can be appreciated that such measurement parameters and values are exemplary only and are not limiting features of the disclosed embodiments.

Note that the term firmware as utilized herein refers to permanent software programmed into a read-only memory. In electronic systems and computing, firmware is a type of software that provides control, monitoring, and data manipulation of engineered products and systems. Examples of devices containing firmware are embedded systems (e.g., traffic lights, consumer appliances, remote controls, digital watches, etc.), computers, computer peripherals, mobile phones and tablets computing devices, digital cameras, etc. The firmware contained in these devices provides a low-level control program for the device. Firmware is capable of being updated.

Firmware can be held in non-volatile memory devices, such as ROM, EPROM of Flash memory. Changing the firmware of a device may rarely or never be done during its lifetime; some firmware memory devices are permanently installed and cannot be changed after manufacture. Common reasons for updating firmware include fixing bugs or adding features to the device. This may require ROM integrated circuits to be physically replaced, or flash memory to be reprogrammed through a special procedure. Firmware such as the ROM BIOS of a personal computer may contain only elementary basic functions of a device and may only provide services to higher-level software. Firmware such as the program of an embedded system may be the only program that will run on the system and provide all of its functions. In the example embodiments discussed herein, the transmitter firmware discussed above can be firmware associated with the GWR transmitter 8.

The GWR component 12 is thus a guided wave radar level measurement device that includes the GWR transmitter 8 and the GWR probe 13, which can be utilized to measure the level of a product in the vessel 14, along with properties of substances in the vessel such as the aforementioned hydrocarbon/salt mixture. The GWR transmitter 8 associated with the GWR component 12 sends a short pulse of RF energy along a waveguide and measures the time of flight of the signals reflected from the surface and interfaces of the products in the vessel. Such waveguides can be constructed of steel and come in rope, rod, and coaxial types. Chemical compatibility and physical strength must be considered because the waveguide must come into physical contact with the product.

One non-limiting example of a GWR component/transmitter that can be utilized to implement the GWR component 12 is disclosed in U.S. Patent Application Publication No. 20160320223 entitled "Streamlined Probe for Guided Wave Radar Measurement" to Stuart James Heath, et al., which published on Nov. 3, 2016 and is assigned to Honeywell International Inc., and is incorporated herein by reference in its entirety. Another non-limiting example of GWR devices and techniques which can be adapted for use to implement the GWR component 12 is disclosed in U.S. Patent Application Publication No. 20160266240 entitled "Apparatus and Method for Adjusting Guided Wave Radar Pulse Width to Optimize Measurements," which published on Sep. 15, 2016 to Michael Kon Yew Hughes, et al., and is also assigned to Honeywell International Inc., and is also incorporated herein by reference in its entirety.

Figure 2:
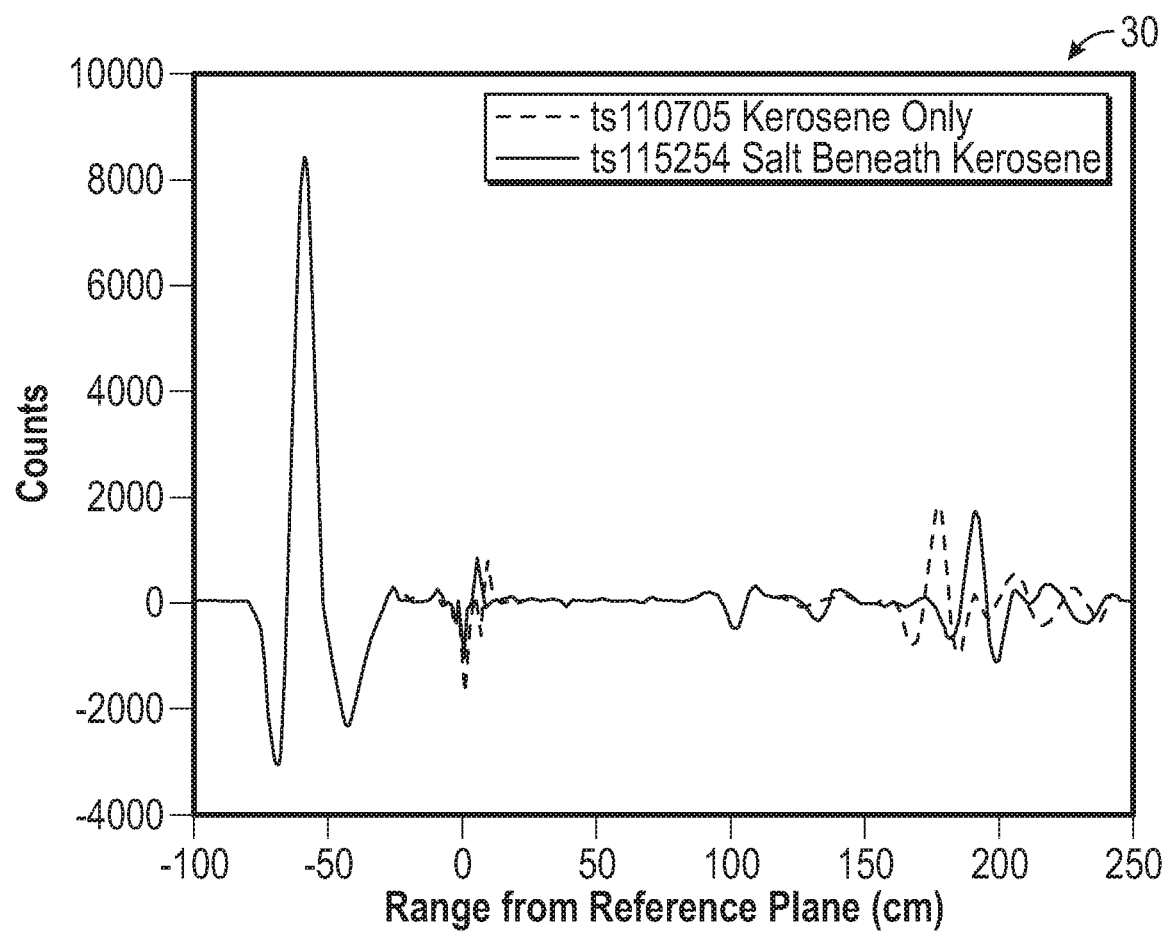
FIG. 2 illustrates a graph depicting data indicative of salt (at approximately 125 cm) beneath kerosene, in accordance with an experimental embodiment.
Figure 3:
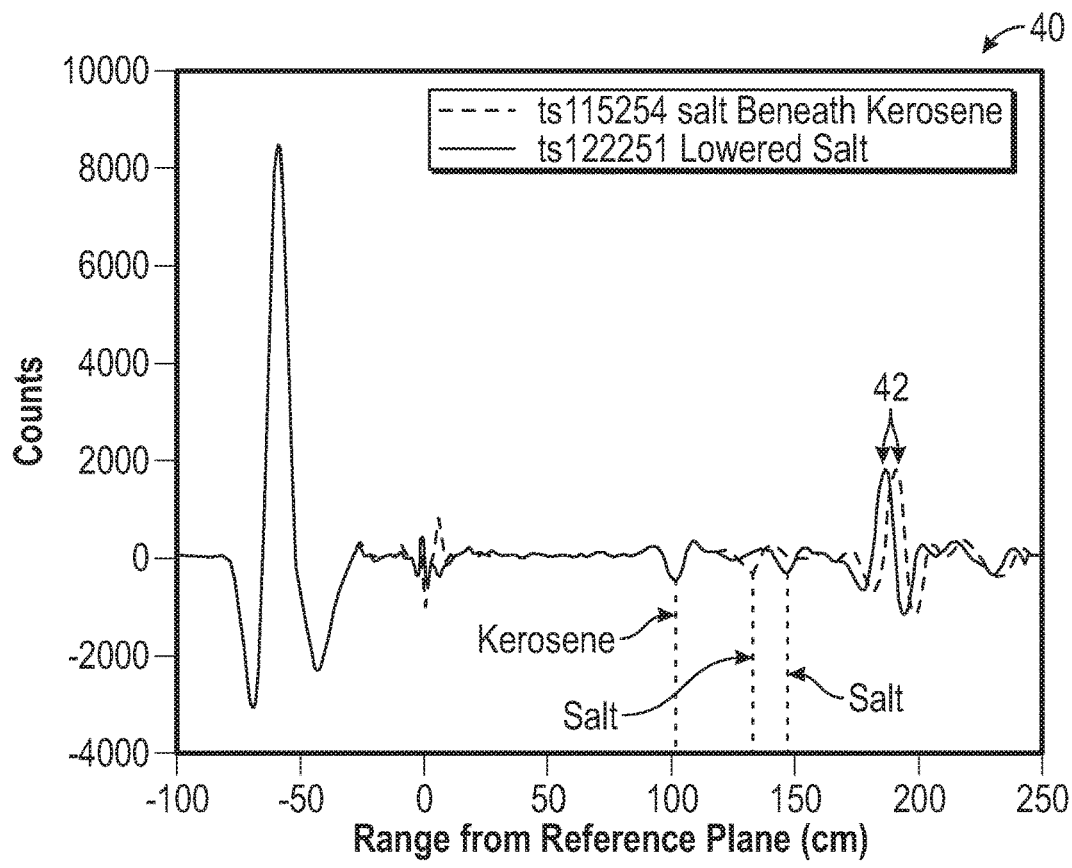
FIG. 3 illustrates a graph depicting data indicative of two salt levels submerged in kerosene, in accordance with an experimental embodiment.
Figure 4:
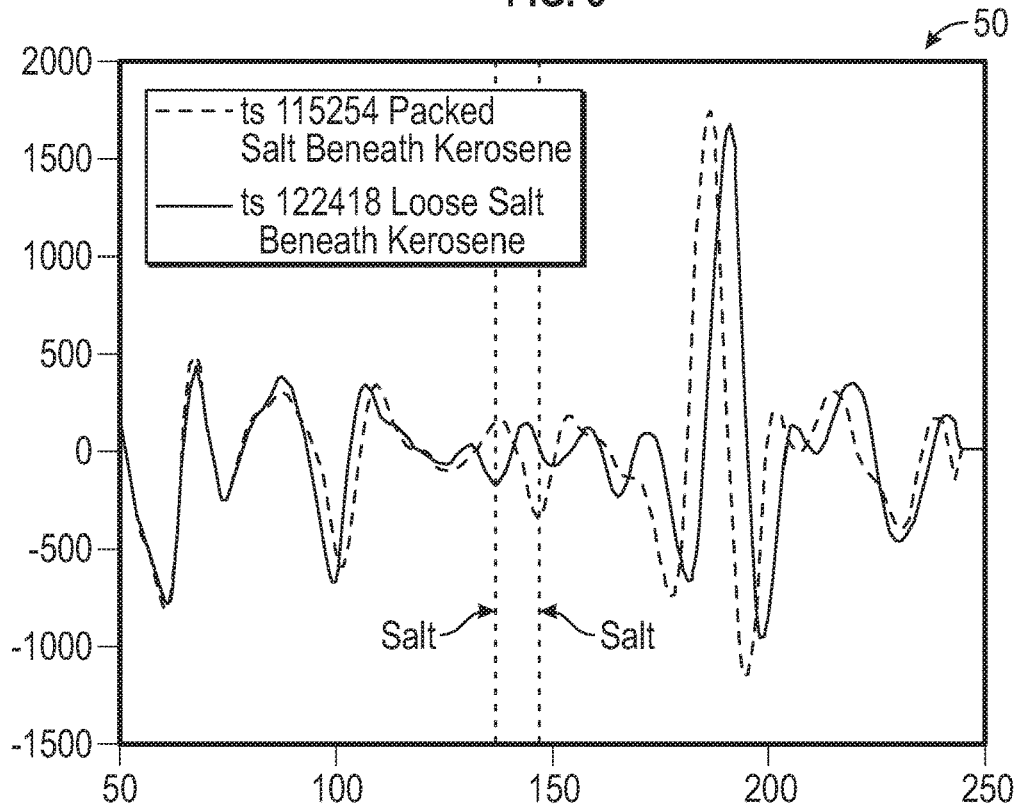
FIG. 4 illustrates a graph depicting data indicative of a reduced reflection from a non-even salt surface, in accordance with an experimental embodiment.

FIGS. 2-4 are provided herein to illustrate data collected as part of various experimental tests of the system 10. Such data is not considered a limiting feature of the disclosed embodiments. Instead, such data is provided for general exemplary purposes only. The objective of such experimental testing was to determine if a salt interface could be seen in a kerosene vessel, such as, for example, the vessel 14. Measurements were taken to predict when salt would need to be replaced in a kerosene (or diesel) dryer.

FIG. 2 illustrates a graph 30 depicting data indicative of salt (e.g., at approximately 130 cm observed distance) beneath kerosene, in accordance with an experimental embodiment. FIG. 3 illustrates a graph 40 depicting data indicative of two salt levels submerged in kerosene, in accordance with an experimental embodiment. The data in graph 30 of FIG. 2 indicates that the salt level can be seen quite clearly beneath the kerosene and the data in graph 40 of FIG. 3 shows two different salt levels. FIG. 2 and FIG. 3 also illustrate that the level of salt can be determined from measurements of the end of probe position. An example of an end of probe position is shown as the end of probe position(s) 42 in graph 40 of FIG. 3.

FIG. 4 illustrates a graph 50 depicting data indicative of a reduced reflection from a non-even salt surface, in accordance with an experimental embodiment. The GWR transmitter can resolve surfaces to 1-mm resolution, and the width of the echos is approximately 100 mm. Features between these length scales can cause measurement issues. The data in graph 50 in FIG. 4 indicates a much reduced reflection from a non-even salt surface. This type of reflection can be difficult to identify reliably. The disclosed approach for measuring the amount of salt in the vessel involves looking at the position of the end of probe reflection. The more salt that is in the vessel, the further away the end of the probe reflection will appear.

The end or lower portion of the probe reflection is the large positive peak, and is very easily identifiable. This method is insensitive to the density of salt or the quality of the surface. To employ this method, 1) the end of the probe 13 would have to be kept higher than any brine level in the vessel (a brine level would show up as a large negative peak and the end of the probe would not be visible), and 2) the attenuation of the GWR of the GWR component 12 would have to be small enough for the end of probe 13 to be visible in a full vessel.

The end-of-probe position can be identified by a peak-detection algorithm or in some example embodiments by a correlation method such as disclosed in U.S. Patent Application Publication No. US20160097669A1 entitled "Level Finding Using Multiple Search Steps," which published to Backstrom et al., on Apr. 7, 2016 and is assigned to Honeywell International Inc. U.S. Patent Application Publication No. US20160097669A1 is incorporated herein by reference in its entirety.

Figure 5:
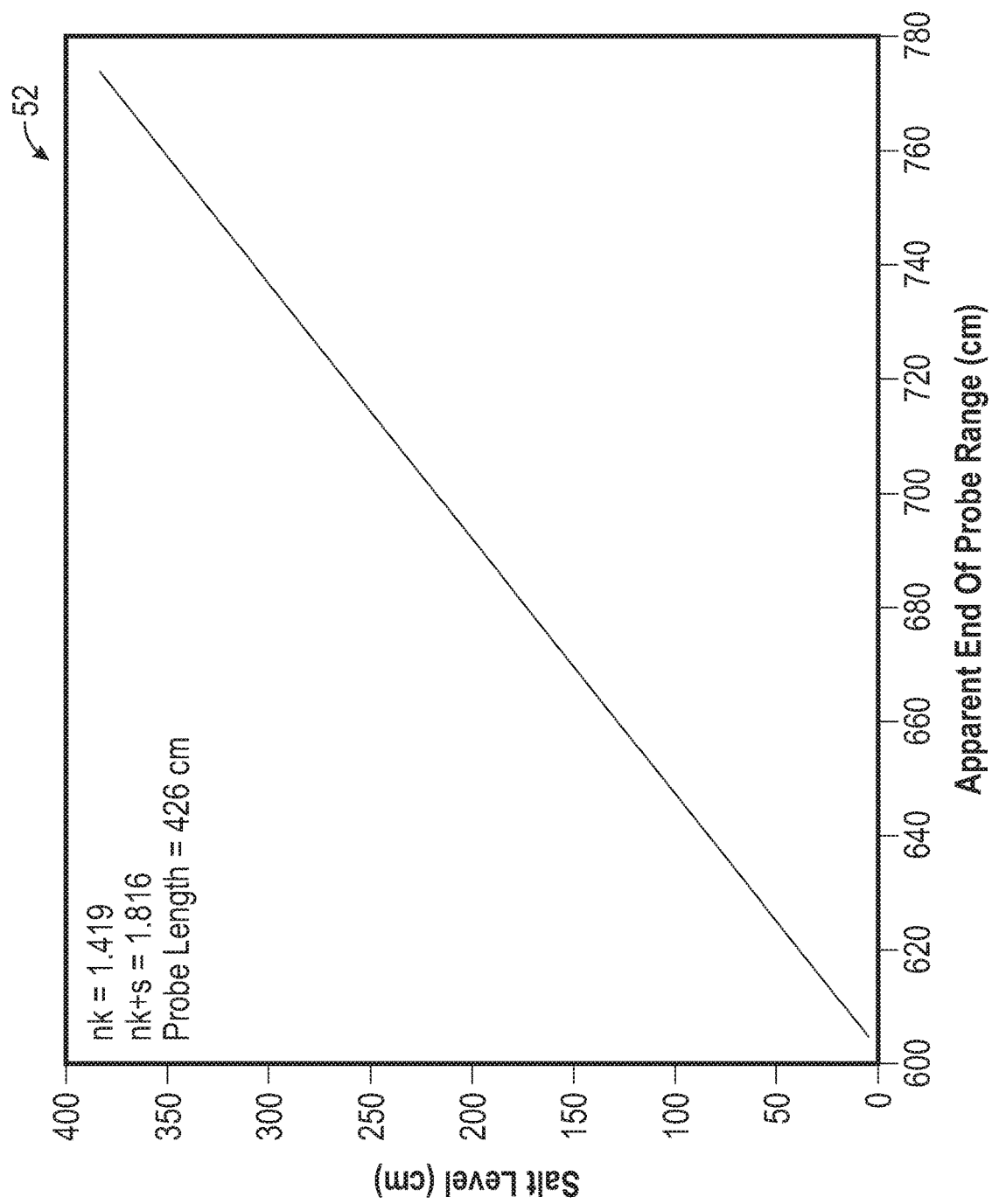
FIG. 5 illustrates a graph depicting data providing an estimation of salt level in kerosene, in accordance with an example embodiment.
Figure 6:
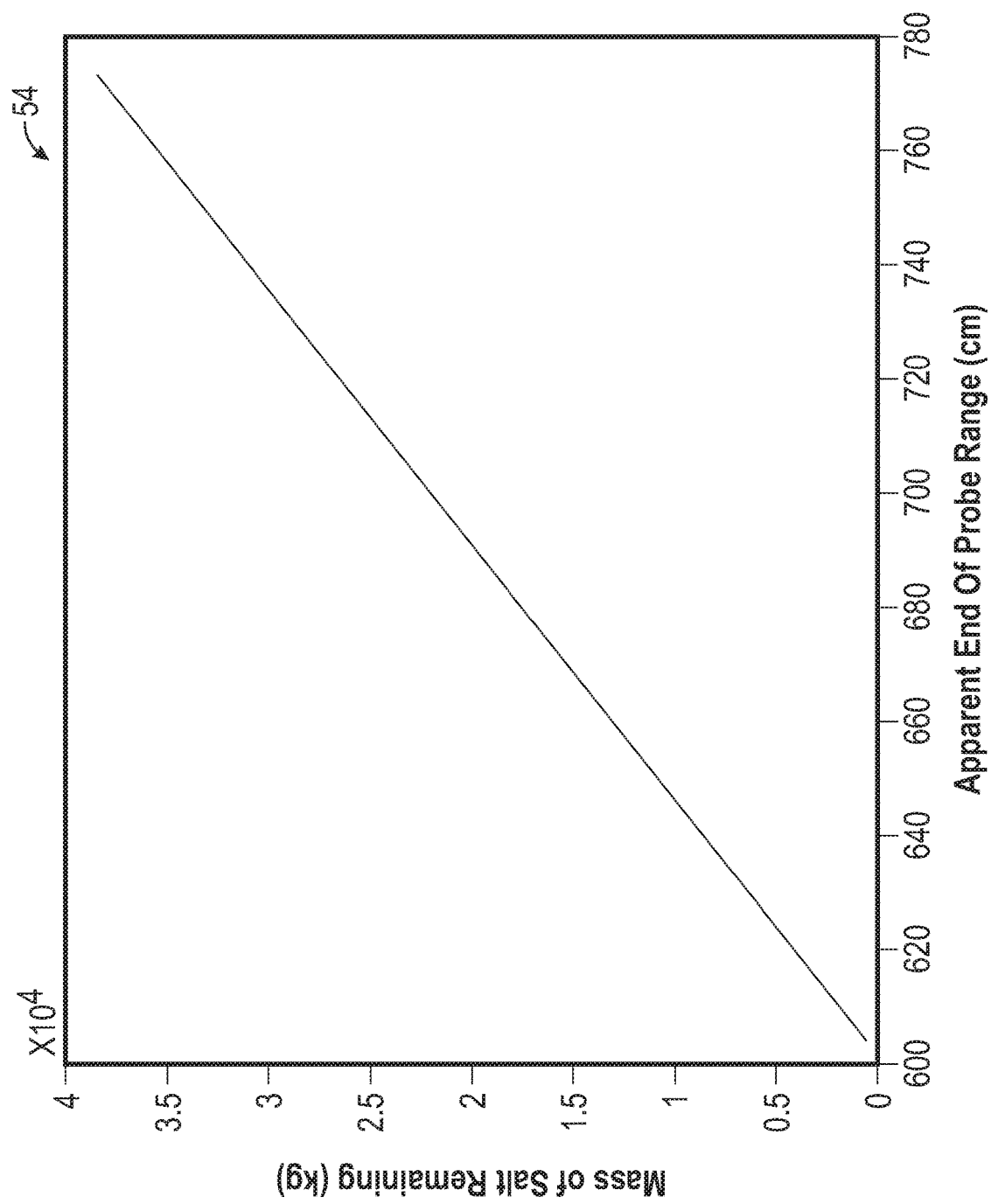
FIG. 6 illustrates a graph depicting data calculating the mass of salt remaining from an apparent end or probe range, in accordance with an example embodiment.

Additional experimental data is shown in FIGS. 5-6. FIG. 5 illustrates a graph 52 depicting data providing an estimation of salt level in kerosene, in accordance with an example embodiment. Graph 52 plots data indicative of the salt level in centimeters (Y-Axis) versus apparent end of probe range data (X-Axis). FIG. 6 illustrates a graph 54 depicting data calculating the mass of salt remaining from an apparent end or probe range, in accordance with an example embodiment. In graph 54 of FIG. 6, the mass of salt remaining is plotted (Y-Axis) versus the apparent end of probe range (X-Axis).

Figure 7:
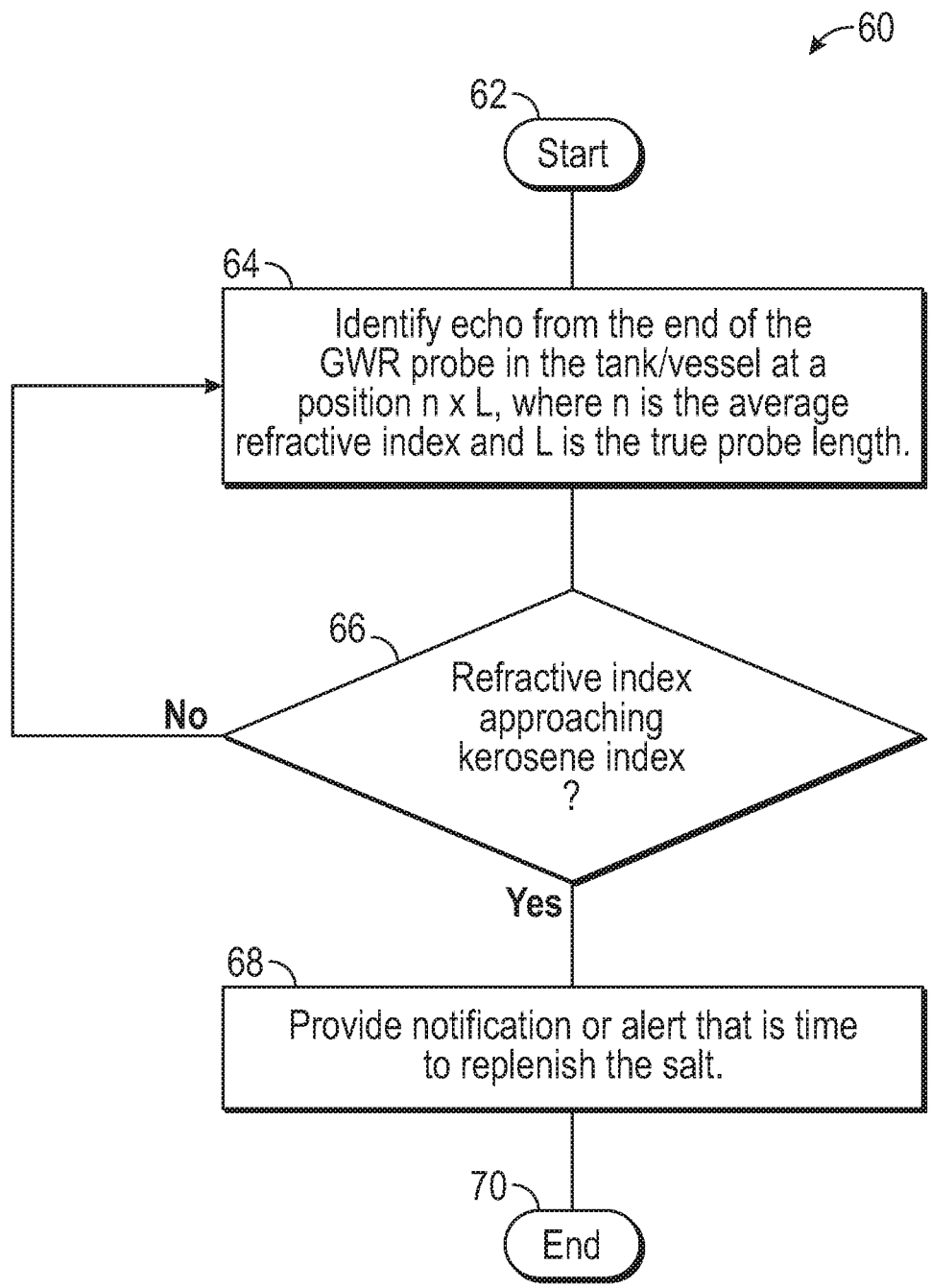
FIG. 7 illustrates a method for monitoring the level of salt in a salt dryer vessel, in accordance with an example embodiment.

FIG. 7 illustrates a method 60 for monitoring the level of salt in a salt dryer vessel, in accordance with an example embodiment. As indicated at block 62, the process begins. Then, as indicated at block 64, a step, operation, or instruction can be implemented to identify the echo from the end of a GWR probe (such as shown in FIG. 1). This will be at a position n×L, where n is the average refractive index and L is the true probe length. A test can then be performed, as shown at decision block 66, to determine if the refractive index measured is approaching the refractive index of the kerosene (or other hydrocarbon). If not (the answer is "no" with respect to decision block 66), the monitoring operations continue (e.g., repeating the operation shown at block 64, etc.). If the answer is "yes", then as indicated thereafter at block 68, a step, operation, or instruction can be implemented to provide a notification or alert (e.g., a text alert sent to a smartphone or other computing device, or another form of alert or notification) that it is now time to replenish the salt in the vessel. The process then ends, as indicated at block 70.

Thus, knowing the properties of kerosene and salt, the amount of salt in the vessel can be automatically and easily calculated. The measurement of concern is the average refractive index of the mixture of the hydrocarbon and salt properties. The more salt in the vessel, the higher the refractive index. When the refractive index approaches that of kerosene by itself, it will be time to replenish the salt.

If it is desired to keep the amount of salt in the vessel greater than a certain quantity to maintain water extraction efficiency, then a set point can be made such that when the processed measurement crosses a threshold, salt replenishment can be triggered.

Note that for two material compositions such as where one is a liquid and the other is a liquid plus a solid (e.g., salt and salt plus kerosene) in the vessel 14, a calculation can be performed as follows. To begin with, we would like to know the distance to the interface between the two material compositions. The interface reflection may or may not be visible. The end-of-probe reflection is visible and identifiable with an end-of-probe model as has already been defined. The dielectric constants (DC) of the first and second media are known. Also the Probe length, PL, is known. We find that the true distance to the interface, $$dtp = \frac{d(EoP) - n_2 \cdot PL}{n_1 - n_2},$$

where $d(EoP)$ is the apparent End of Probe position relative to the reference plane, and $n=\sqrt{DC}$, $n_1$ denotes the upper material and $n_2$ the lower.

When there are two materials, we can assume that there are two regions with well-known dielectric constants. In a salt drier, the vessel is initially filled with salt to a certain level, and the remaining space, on top of the salt and in between the salt pieces is filled with kerosene. The dielectric constant of the kerosene is well known and so is the dielectric constant of a packed salt+kerosene mix. It is easier to work with indices of refraction (n) rather than dielectric constants (DC): $n^2$=DC. The index of kerosene is $n_k$ and that of packed salt in kerosene is $n_s$. To illustrate this, refer to the previously discussed graph 52 of FIG. 5, which is based on actual data providing an estimation of the salt level in kerosene.

Initially when the salt drier is loaded, the surface of the salt submerged in kerosene is likely very detectable. If there is some uncertainty in the DC of the salt in kerosene, it can be estimated at this time with knowledge of the position of the interface, from the interface reflection, and the true probe length.

The function of the salt is to absorb water in the hydrocarbon. As it does so, the solid salt will become brine and will flow to the bottom of the vessel from where it can be drained. As the salt is removed, it becomes less dense, and with settling, the surface of the salt becomes less defined. This means both that the salt surface reflection will become less defined and that the dielectric constant of the salt in the kerosene will change. We are, however, more concerned with the amount of salt in the vessel rather than the exact level because this better defines when maintenance must be scheduled to add more salt (i.e., it is a measure of how much salt has been consumed). From such considerations, we can monitor the end of probe position as follows: d(EoP)=n.sub-.kt.sub.k+n'.sub.st.sub.s, where n'.sub.s is the actual index of the salt kerosene mix.

We can approximate this index as $n'_s = f_k \cdot n_k + f_s \cdot n_s$ (Equation 1). Here, $n_s$ is the index of pure salt, $f_k$ and $f_s$ are the volume fractions of kerosene and salt, respectively. If this equation describes the index adequately, then the end of probe position describes the amount of salt in the vessel. This is a reasonable approximation for these material given that the salt particles are large. Graph 54 in FIG. 6 discussed previously, for example, shows how the mass of salt remaining in the vessel can be calculated from the apparent end-of-probe position. Note that this conversion may be done automatically in the transmitter, but it is more likely to be done by configuring the transmitter to output an effective salt level, and then using a computer interface to multiply the volume by the density to get a mass.

Often, a user is more interested in converting the output to a percentage. This is especially true if the output is provided by, for example, an analog 4-20 mA signal. In this particular scenario, the maximum salt level (URV=upper range value) can be set to 100% and the zero level (LRV=lower range value) set to 0%.

Also note that Equation 1 may not exactly describe the index of refraction of a salt kerosene mix as the mass fraction is changing. Equation 1, however, represents a likely and good approximation. One method for estimating the amount of salt in the vessel 14 can be implemented as follows:

1. Configure the GW transmitter to produce an output of salt level or a signal proportional to the salt level based on a best guess index of refraction for salt+kerosene (the kerosene index must be known)
2. Start with a vessel filled with kerosene but no salt, and determine the apparent probe length, or calculate this knowing the kerosene index of refraction. Set this output value to be the LRV.
3. Fill the vessel with salt and then with kerosene; set this value to be the URV.
4. If desired, a monitoring computer system (e.g., such as the monitoring or control system 11) can be programmed to then estimate the amount of salt in the vessel using a linear relation and knowledge of the amount of salt added.
5. As the amount of salt is reduced, the output will be at least roughly approximate to the amount of salt in the vessel. The measurement will be more accurate near the vessel full and vessel empty positions.

Alternatively, the relationship between salt mass fraction and index of refraction can be determined and the relation entered into a computer program to more exactly give an estimate of the amount of salt in the vessel.

The disclosed embodiments offer a number of advantages. For example, automated measurements are currently not available. Thus, implementation of the various embodiments described herein can save a great deal of expense and time, while also eliminating the risk of unscheduled shutdowns, which may be possible if there is no salt or other solid consumable in the dryer (e.g., kerosene dryers, diesel dryers, etc.).

As can be appreciated by one skilled in the art, embodiments can be implemented in the context of a method, data processing system, or computer program product. Accordingly, embodiments may take the form of an entire hardware embodiment, an entire software embodiment, or an embodiment combining software and hardware aspects all generally referred to herein as a "circuit" or "module." Furthermore, embodiments may in some cases take the form of a computer program product on a computer-usable storage medium having computer-usable program code embodied in the medium. Any suitable computer readable medium may be utilized including hard disks, USB Flash Drives, DVDs, CD-ROMs, optical storage devices, magnetic storage devices, server storage, databases, etc.

Computer program code for carrying out operations of the present invention may be written in an object-oriented programming language (e.g., Java, C++, etc.). The computer program code, however, for carrying, out operations of particular embodiments may also be written in conventional procedural programming languages, such as the "C" programming language or in a visually oriented programming environment, such as, for example, Visual Basic.

The program code may execute entirely on the user's computer, partly on the user's computer, as a stand-alone software package, partly on the user's computer and partly on a remote computer, or entirely on the remote computer. In the latter scenario, the remote computer may be connected to a user's computer through a local area network (LAN) or a wide area network (WAN), wireless data network e.g., Wimax, 802.xx, and cellular network or the connection may be made to an external computer via most third party supported networks (for example, through the Internet utilizing an Internet Service Provider).

The embodiments are described at least in part herein with reference to flowchart illustrations and/or block diagrams of methods, systems, and computer program products and data structures according to embodiments of the invention. It will be understood that each block of the illustrations, and combinations of blocks, can be implemented by computer program instructions. These computer program instructions may be provided to a processor of, for example, a general-purpose computer, special-purpose computer, or other programmable data processing apparatus to produce a machine, such that the instructions, which execute via the processor of the computer or other programmable data processing apparatus, create means for implementing the functions/acts specified in the block or blocks. To be clear, the disclosed embodiments can be implemented in the context of, for example, a special-purpose computer or a general-purpose computer, or other programmable data processing apparatus or system. For example, in some embodiments, a data processing apparatus or system can be implemented as a combination of a special-purpose computer and a general-purpose computer.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the various block or blocks, flowcharts, and other architecture illustrated and described herein.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
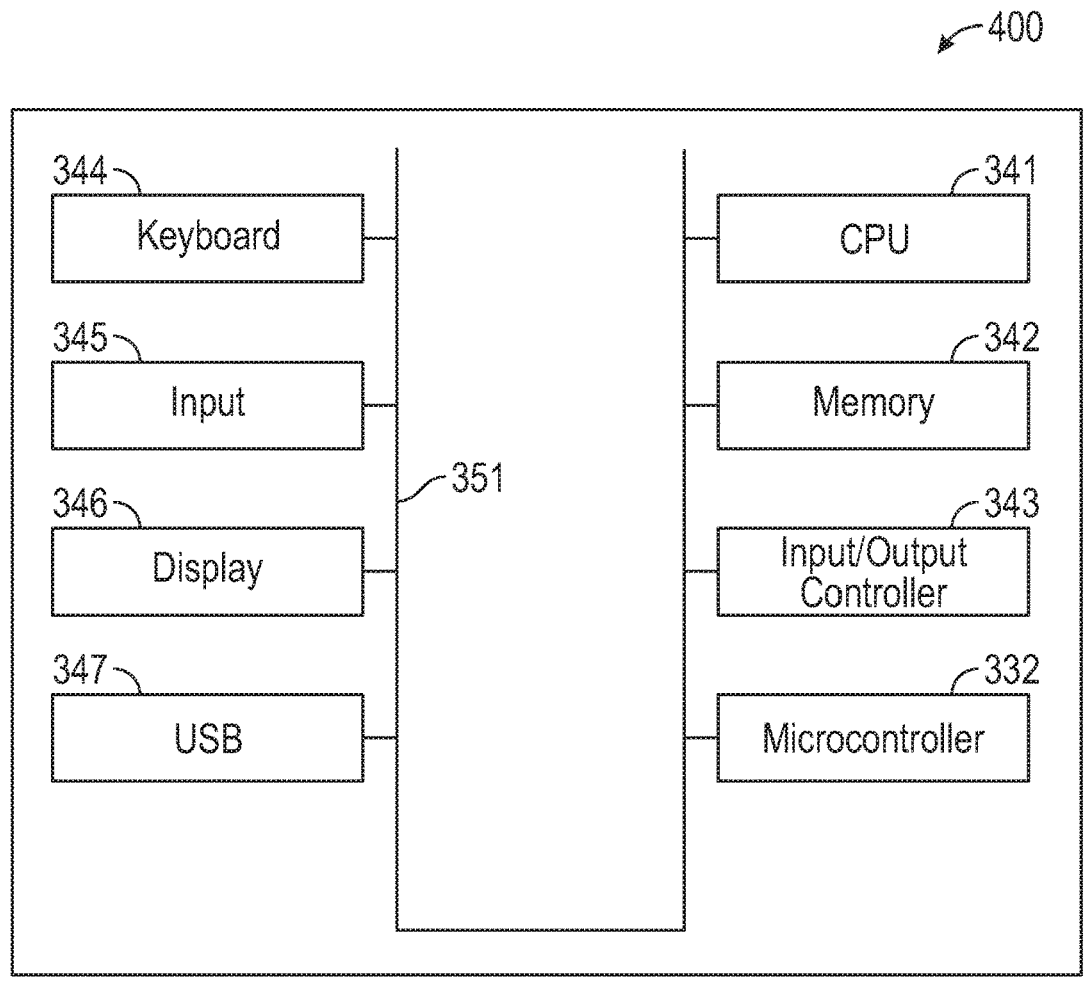
FIG. 8 illustrates a schematic view of a computer system/ apparatus, which can be implemented in accordance with an example embodiment.
Figure 9:
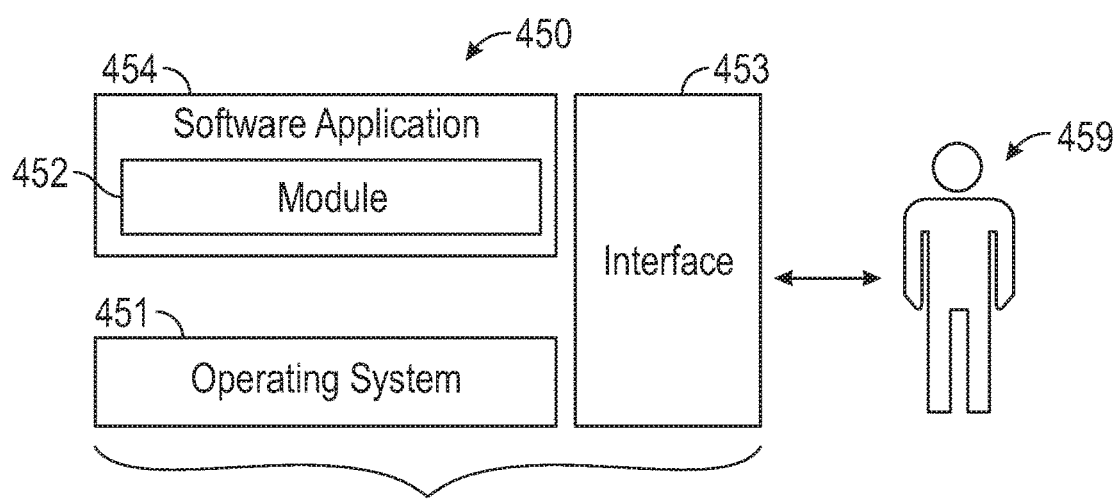
FIG. 9 illustrates a schematic view of a software system including a module, an operating system, and a user interface, which can also be implemented in accordance with an example embodiment.

FIGS. 8-9 are shown only as exemplary diagrams of data-processing environments in which example embodiments may be implemented. It should be appreciated that FIGS. 8-9 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

As illustrated in FIG. 8, some embodiments may be implemented in the context of a data-processing system/apparatus 400 that can include, for example, one or more processors such as a processor 341 (e.g., a CPU (Central Processing Unit) and/or other microprocessors), a memory 342, an input/output controller 343, a microcontroller 332, a peripheral USB (Universal Serial Bus) connection 347, a keyboard 344 and/or another input device 345 (e.g., a pointing device, such as a mouse, track ball, pen device, etc.), a display 346 (e.g., a monitor, touch screen display, etc.), and/or other peripheral connections and components.

As illustrated, the various components of data-processing system/apparatus 400 can communicate electronically through a system bus 351 or similar architecture. The system bus 351 may be, for example, a subsystem that transfers data between, for example, computer components within data-processing system/apparatus 400 or to and from other data-processing devices, components, computers, etc. The data-processing system/apparatus 400 may be implemented in some embodiments as, for example, a server in a client-server based network (e.g., the Internet) or in the context of a client and a server (i.e., where aspects are practiced on the client and the server).

In other example embodiments, data-processing system/apparatus 400 may be, for example, a standalone desktop computer, a laptop computer, a Smartphone, a pad computing device and so on, wherein each such device is operably connected to and/or in communication with a client-server based network or other types of networks (e.g., cellular networks, Wi-Fi, etc.). In still other example embodiments, the apparatus 400 may provide and facilitate the transmitter firmware discussed herein. The data-processing system/apparatus 400 can be used, for example, to implement the monitoring or control system 11 of FIG. 1.

FIG. 9 illustrates a computer software system/apparatus 450 for directing the operation of the data-processing system/apparatus 400 depicted in FIG. 8. Software application 454, stored for example in memory 342, generally includes a kernel or operating system 451 and a shell or interface 453. One or more application programs, such as software application 454, may be "loaded" (i.e., transferred from, for example, mass storage or another memory location into the memory 342) for execution by the data-processing system/apparatus 400. The data-processing system/apparatus 400 can receive user commands and data, through the interface 453; these inputs may then be acted upon by the data-processing system/apparatus 400 in accordance with instructions from operating system 451 and/or software application 454. The interface 453 in some embodiments can serve to display results, whereupon a user 459 may supply additional inputs or terminate a session. The software application 454 can include module(s) 452, which can, for example, implement the various instructions or operations such as those discussed herein with respect to FIGS. 1-7 herein. Module 452 may also be composed of a group of modules or sub-modules that implement particular instructions, steps, or operations, such as discussed and illustrated herein with respect to FIGS. 1-7.

The following discussion is intended to provide a brief, general description of suitable computing environments in which the system and method may be implemented. Although not required, the disclosed embodiments will be described in the general context of computer-executable instructions, such as program modules, being executed by a single computer. In most instances, a "module" can constitute a software application, but can also be implemented as both software and hardware (i.e., a combination of software and hardware).

Generally, program modules include, but are not limited to, routines, subroutines, software applications, programs, objects, components, data structures, etc., that perform particular tasks or implement particular data types and instructions. Moreover, those skilled in the art will appreciate that the disclosed method and system may be practiced with other computer system configurations, such as, for example, hand-held devices, multi-processor systems, data networks, microprocessor-based or programmable consumer electronics, networked PCs, minicomputers, mainframe computers, servers, and the like.

Note that the term module as utilized herein may refer to a collection of routines and data structures that perform a particular task or implements a particular data type. Modules may be composed of two parts: an interface, which lists the constants, data types, variable, and routines that can be accessed by other modules or routines; and an implementation, which is typically private (accessible only to that module) and which includes source code that actually implements the routines in the module. The term module may also simply refer to an application, such as a computer program designed to assist in the performance of a specific task, such as word processing, accounting, inventory management, etc.

FIGS. 8-9 are thus intended as examples and not as architectural limitations of disclosed embodiments. Additionally, such embodiments are not limited to any particular application or computing or data processing environment. Instead, those skilled in the art will appreciate that the disclosed approach may be advantageously applied to a variety of systems and application software. Moreover, the disclosed embodiments can be embodied on a variety of different computing platforms, including Macintosh, UNIX, LINUX, and the like.

Based on the foregoing, it can be appreciated that a number of example embodiments are disclosed. For example, in one embodiment, a method for monitoring amounts of a submerged solid consumable (e.g., salt, etc.) can be implemented. Such a method can includes steps, instructions or operations such as, for example, measuring with a GWR (Guided Wave Radar) component a measurement of a reflection at a fixed position in a particle bed such that the reflection represents aggregate dielectric properties in a vessel, wherein the measurement includes hydrocarbon and solid consumable properties of a mixture in the vessel. A measurement value of the measurement is indicative of a greater amount of the solid consumable in the mixture in the vessel. In some example embodiments, if data is measured by the GWR component indicating that the measurement value approaches a measurement value of the hydrocarbon, the data is indicative that a material in the vessel should be replenished.

In some example embodiments, the hydrocarbon can be, for example, kerosene, diesel, naphtha, or LPG (Liquefied Petroleum Gas). In some example embodiments, the aforementioned vessel may be a salt dryer. In other example embodiments, the aforementioned solid consumable can be, for example, salt containing sodium chloride, potassium chloride, calcium chloride, or lithium chloride, or a combination thereof. In yet other example embodiments, the hydrocarbon can comprise of, for example, butane, propane, or alkylates and the mixture can be composed of, for example, potassium hydroxide, or calcium hydroxide.

In another example embodiment, a step or operation can be implemented for identifying the echo from the end of the GWR component located at a position n×L, wherein n comprises the effective refractive index and L comprises the length of the GWR component. In addition, a step or operation can be implemented for calculating the amount of solid consumable in the vessel based on the properties of the hydrocarbon and the solid consumable and the n and the L.

In another example embodiment, the aforementioned GWR component can include a transmitter and transmitter firmware associated with the transmitter, wherein the transmitter firmware identifies the echo. The GWR component also preferably includes a GWR probe. In another example embodiment, a step or operation can be provided for automatically maintaining an amount of solid consumable in the vessel above a predetermined level using a monitoring and control system.

In another example embodiment, an apparatus for monitoring amounts of submerged solid consumable can be implemented, which includes a GWR (Guided Wave Radar) component that provides a measurement of a reflection at a fixed position in a particle bed such that the reflection represents aggregate dielectric properties in a vessel, wherein the measurement includes hydrocarbon and solid consumable properties of a mixture in the vessel, wherein a measurement value of the measurement is indicative of a greater amount of solid consumable in the mixture in the vessel, and wherein if data is measured by the GWR component indicating that the measurement value approaches a measurement value of the hydrocarbon, the data is indicative that a material in the vessel should be replenished.

In still another example embodiment, a system for monitoring amounts of submerged solid consumable can be implemented. Such a system can include, for example: a GWR (Guided Wave Radar) component that provides a measurement of a reflection at a fixed position in a particle bed such that the reflection represents aggregate dielectric properties in a vessel, wherein the measurement includes hydrocarbon and solid consumable properties of a mixture in the vessel, wherein a measurement value of the measurement is indicative of a greater amount of solid consumable in the mixture in the vessel, and wherein if data is measured by the GWR component indicating that the measurement value approaches a measurement value of the hydrocarbon, the data is indicative that a material in the vessel should be replenished; and a monitoring and control system for automatically maintaining an amount of solid consumable in the vessel above a predetermined level based on the measurement.

The foregoing description of the embodiments has been provided for purposes of illustration and description. It is not intended to be exhaustive or to limit the disclosure. Individual elements, or features of a particular embodiment are generally not limited to that particular embodiment, but, where applicable, are interchangeable and can, be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A method for monitoring amounts of submerged solid consumable, said method comprising:
    identifying an echo from an end of a GWR (Guided Wave Radar) component located at a position n×L, wherein n comprises an effective refractive index and L comprises a length of said GWR component;
    measuring with the GWR component, a measurement of a reflection at a fixed position in a particle bed such that said reflection represents an aggregate dielectric constant in a vessel, wherein said measurement involves determining when the effective refractive index measured is approaching a refractive index of hydrocarbon in a liquid mixture of the hydrocarbon and a solid consumable, wherein the measurement includes the effective refractive index of the liquid mixture that includes the hydrocarbon and the solid consumable which is supported on a screen located above a lower portion of said vessel, and said fixed position of said GWR component is placed above said screen; and calculating an amount of said solid consumable in said vessel based on properties of said hydrocarbon and said solid consumable and based on said n and said L.

2. The method of claim 1 wherein said hydrocarbon comprises at least one of kerosene, diesel, naphtha, and LPG (Liquefied Petroleum Gas).

3. The method of claim 1 wherein said vessel comprises a salt dryer.

4. The method in claim 1 wherein said solid consumable comprises salt containing sodium chloride, calcium chloride, or lithium chloride, or a combination thereof.

5. The method of claim 1 wherein said hydrocarbon comprises at least one of butane, propane, or alkylates and said mixture comprises at least one of potassium hydroxide or calcium hydroxide.

6. The method of claim 1 wherein a measurement value measured by said GWR component approaches a predetermined measurement value, said data is indicative that a material in said vessel should be replenished.

7. The method of claim 6 wherein said GWR component includes a GWR probe, a GWR transmitter, and transmitter firmware associated with said GWR transmitter, wherein said transmitter firmware identifies said echo.

8. The method of claim 1 further comprising automatically maintaining an amount of solid consumable in said vessel above a predetermined level using a monitoring and control system.

9. An apparatus for monitoring amounts of submerged solid consumable, said apparatus comprising:

a GWR (Guided Wave Radar) component that provides a measurement of a reflection at a fixed position in a particle bed such that said reflection represents aggregate dielectric constant in a vessel, wherein said measurement wherein said measurement involves determining when the effective refractive index measured is approaching an effective refractive index of a hydrocarbon in liquid mixture of the hydrocarbon and a solid consumable, and wherein said measurement includes the effective refractive index of said liquid mixture that includes the hydrocarbon and the solid consumable which is supported on a screen located above a lower portion of said vessel, and said fixed position of said GWR component is placed above said screen, and wherein a measurement value of said measurement is indicative of the amount of said solid consumable in said mixture in said vessel; and wherein an echo is identified from an end of said GWR component located at a position n×L, wherein n comprises an effective refractive index and L comprises a length of said GWR component and wherein an amount of said solid consumable is calculated in said vessel based on properties of said hydrocarbon and said solid consumable based on and said n and said L.

10. The apparatus of claim 9 wherein said hydrocarbon comprises at least one of kerosene, diesel, naphtha, and LPG (Liquefied Petroleum Gas).

11. The apparatus of claim 9 wherein said vessel comprises a salt dryer.

12. The apparatus in claim 9 wherein said solid consumable comprises salt containing sodium chloride, calcium chloride, or lithium chloride, or a combination thereof.

13. The apparatus of claim 9 wherein said hydrocarbon comprises at least one of butane, propane, or alkylates and said mixture comprises at least one of sodium hydroxide, potassium hydroxide, or calcium hydroxide.

14. The apparatus of claim 9 wherein if data is measured by said GWR component indicating that said measurement value approaches a measurement value of said hydrocarbon, said data is indicative that a material in said vessel should be replenished.

15. The apparatus of claim 9 wherein said GWR component includes a transmitter and transmitter firmware associated with said transmitter, wherein said transmitter firmware identifies said echo.

16. A system for monitoring amounts of submerged solid consumable, said system comprising:

a GWR (Guided Wave Radar) component that provides a measurement of a reflection at a fixed position in a particle bed such that said reflection represents aggregate dielectric constant in a vessel, wherein said measurement determines when the effective refractive index measured is approaching an effective refractive index of a hydrocarbon in a liquid mixture that includes the hydrocarbon and a solid consumable, and wherein said measurement includes the effective refractive index of the liquid mixture that includes the hydrocarbon and the solid consumable which is supported on a screen located above a lower portion of said vessel, and said fixed position of said GWR component is placed above said screen, wherein a measurement value of said measurement is indicative of the amount of said solid consumable in said mixture in said vessel, and wherein if data is measured by said GWR component indicating that said measurement value approaches a measurement value of said hydrocarbon, said data is indicative that a material in said vessel should be replenished;

a monitoring and control system for automatically maintaining an amount of solid consumable in said vessel above a predetermined level based on said measurement; and wherein an echo is identified from an end of said GWR component located at a position n×L, wherein n comprises an effective refractive index and L comprises a length of said GWR component, and wherein an amount of said solid consumable is calculated in said vessel based on properties of said hydrocarbon and said solid consumable and based on said n and said L.

* * * * *